United States Patent [19]

Glantschnig

[11] Patent Number: 4,618,975
[45] Date of Patent: Oct. 21, 1986

[54] METHOD AND APPARATUS FOR ANALYZING A POROUS NONHOMOGENEOUS CYLINDRICAL OBJECT

[75] Inventor: Werner J. Glantschnig, Belle Mead, N.J.

[73] Assignee: AT&T Technologies, Inc., Berkeley Heights, N.J.

[21] Appl. No.: 684,950

[22] Filed: Dec. 21, 1984

[51] Int. Cl.$^4$ ............................................. G01N 23/06
[52] U.S. Cl. ....................................... 378/51; 378/53; 378/54; 378/55; 364/414
[58] Field of Search ....................... 378/53, 54, 55, 56; 364/414

[56] References Cited

U.S. PATENT DOCUMENTS

| 3,414,725 | 12/1968 | Evans | 250/83.3 |
|---|---|---|---|
| 3,435,220 | 3/1969 | Hanken | 250/83.3 |
| 3,499,736 | 3/1970 | Zwaneburg | 23/301 |
| 3,996,471 | 12/1976 | Fletcher et al. | 250/444 |
| 4,095,106 | 6/1978 | Wallace | 250/358 |
| 4,200,792 | 4/1980 | Fanger et al. | 250/359 |
| 4,217,027 | 8/1980 | MacChesney et al. | 350/96.3 |
| 4,227,806 | 10/1980 | Watkins | 356/731 |
| 4,282,433 | 8/1981 | Loffel | 250/356 |
| 4,284,895 | 8/1981 | Morgan et al. | 250/445 |
| 4,330,835 | 5/1982 | Gehm | 364/560 |

FOREIGN PATENT DOCUMENTS 2088050  6/1982  United Kingdom .................. 378/53

OTHER PUBLICATIONS

"Tomography: An Overview of the AECL Program" by Allan et al. Applied Optics, vol. 24, #23, 12/1/85.
"Tomography for Properties of Materials that Bend Rays: A Tutorial by Charles M. Vest Applied Optics, vol. 24, #23, 12/1/85.
"Mathematical Foundations of Computed Tomography" by Smith et al. Applied Optics, vol. 24, #23, 12/1/85.
"Method of Inspecting Optical Fiber Preforms Using X-Ray Absorption Measurements", H. Takahashi, I. Nakamura, T. Tadatani and T. Kurowa, Japanese Journal Furukawa Denko Jiho, 68, pp. 143–149 (1980).
"Applicative Investigation of X-Ray Non-Destructive Inspection Technique for Measurement of Core Diameters and Germanium Doping Concentration Profiles of Optical Fiber Preforms" by H. Takahashi, et al., published in the Conference Proceedings of the Optical Communications Conference, Sep. 17–19, 1979, Amsterdam, The Netherlands at pp. 14.4-1–14.4-4.

Primary Examiner—Bruce C. Anderson
Assistant Examiner—John C. Freeman
Attorney, Agent, or Firm—R. B. Levy

[57] ABSTRACT

Nondestructive analysis of a porous, inhomogeneous, generally cylindrical object, such as a soot boule (12), comprised of n known components, where n is an integer, is achieved by scanning the boule with a beam (18) comprised of photons, each having a distinct energy within one $n-1$ energy groups. The intensity of the photons within each of the $n-1$ energy groups leaving the boule is detected by a detector (22) and is measured by a pulse height/scaler analyzer (30) at each of a plurality of separate heights $t_i$ of the beam (18) as measured from the center of the boule. A computer (31) determines each of $n-1$ attenuation coefficients $\mu_1(r)$, $\mu_2(r)$, ... $\mu_n(r)$, representing the attenuation of the intensity of the photons in each of the $n-1$ energy groups, respectively, at each height $t_i$ of the beam in accordance with the output data furnished by the scaler/analyzer. From the $n-1$ attenuation coefficients, the computer (31) determines the density $\rho(r)$ and the respective molecular mass fractions $x_1(r), x_2(r) \ldots x_n(r)$ of the n molecular components of the boule (12) at each height $t_i$ of the beam.

8 Claims, 5 Drawing Figures

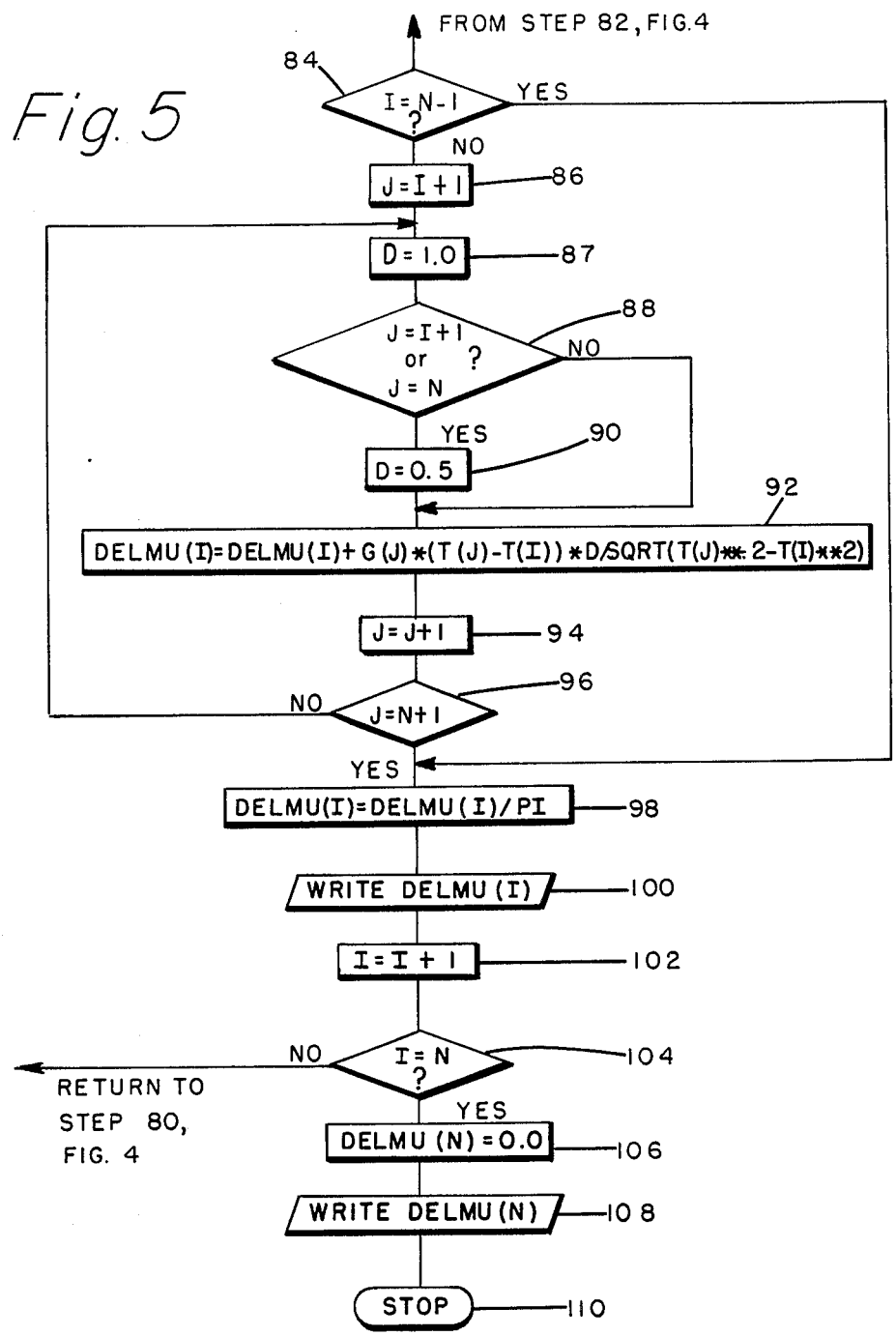

METHOD AND APPARATUS FOR ANALYZING A POROUS NONHOMOGENEOUS CYLINDRICAL OBJECT

TECHNICAL FIELD

This invention relates to a method for nondestructively analyzing a porous, inhomogeneous, generally cylindrical object having n (where n is an integer) known molecular components to determine the density and the mass fraction of each of the n molecular components thereof.

BACKGROUND OF THE INVENTION

Lightguide fiber of the type used to carry communication signals is fabricated by heating and drawing a portion of a lightguide preform comprised of a refractive core surrounded by glass cladding. One process which has proven extremely useful for the fabrication of preforms is the modified chemical vapor deposition technique (MCVD) whereby reactant-containing precursor gases, such as silicon tetrachloride and germanium tetrachloride are passed through the center of a starter tube. As the starter tube is heated and rotated, reaction by-products, in the form of submicron-sized doped glass particles, are deposited on the inside surface of the tube to form the refractive core of the preform. For a further, more detailed description of the MCVD process, reference should be had to U.S. Pat. No. 4,217,027 issued to J. B. MacChesney et al. on Aug. 12, 1980 and assigned to Bell Telephone Laboratories.

Other chemical vapor deposition methods such as the Vapor Phase Axial Deposition (VAD) and the Vapor Phase Radial Deposition (VRD) Techniques are presently being investigated to determine their suitability as potential processes for fabricating lightguide preforms. The VAD and the VRD techniques are both characterized by the deposit of submicron-sized doped glass particles on a bait rod to form a boule. Since the submicron-sized doped glass particles deposited on the bait rod during VAD or VRD processes appear as tiny particles of soot, the term "soot deposition" is often used to describe these two techniques. For the same reason, the boule fabricated by the VAD or VRD process is often referred to as a soot boule.

To fabricate a preform from the soot boule, the boule is first consolidated by sintering. Once sintered, the boule is then cladded by insertion into a silica glass tube. In certain instances, the soot boule may be partially cladded by depositing pure silicon dioxide thereon prior to sintering thereof.

Successful implementation of either the VAD or VRD process on a widespread basis is dependent on the quality of the preforms produced thereby. One useful technique for verifying the quality of the preform is to determine the characteristics, particularly the density and the composition, of the soot boule from which the preform is produced. Since the soot particles comprising the unconsolidated boule are generally opaque to visible light, profiling techniques which rely on the use of visible light such as that disclosed in U.S. Pat. No. 4,227,806 issued to L. S. Watkins on Oct. 14, 1980 and assigned to the assignee of the present invention, are not applicable. At present, analysis of soot boules to determine their suitability for use in the fabrication of lightguide preforms is accomplished by slicing the boule and microscopically examining the cross section thereof. Such an analysis technique renders the boule unsuited for later use.

A recent paper "Method of Inspecting Optical Fiber Preforms Using X-ray Absorption Measurements" by H. Takahashi, I. Nakamura, T. Tadatani and T. Kurowa, published in the Japanese Journal Furukawa Denko Jiho 68, pages 143–149 suggests x-ray absorption techniques used in tomographic applications, can be applied to measure the germanium concentration of preforms. However, the measurement method described in the above-referred paper is believed to be flawed since the authors do not appear to account for the possibility of having an inhomogeneous preform because they fail to disclose any method for measuring the density thereof. Consequently, the accuracy of the germanium concentration measurement obtained by this method is doubtful.

Accordingly, there is a need for a method for accomplishing nondestructive analysis of a soot boule.

BRIEF SUMMARY OF THE INVENTION

The difficulties associated with characterizing the density and the composition of a porous, generally cylindrical, inhomogeneous object, such as a soot boule, comprised of n (where n is an integer), known molecular components, are overcome by the method of the present invention which comprises the steps of: scanning the object with a beam of photons having an axis perpendicular to the axis of the boule, each photon having a distinct energy within one of n−1 energy groups; measuring the intensity of the photons in each energy group upon the passage of the beam through the object at each of a plurality of separate heights $t_i$ of the beam as measured from the axis thereof to the center of the object; establishing each of n−1 attenuation coefficients $\mu_1(r), \mu_2(r) \ldots \mu_{n-1}(r)$ for the object at each height $t_i$ of the beam in accordance with the measured intensity of the photons within each of the n−1 energy groups, respectively; and calculating the density $\rho(r)$ and the mass fractions of each of the n molecular components of the object at each height $t_i$ of the beam in accordance with each of the n−1 attenuation factors $\mu_1(r), \mu_2(r) \ldots \mu_{n-1}(r)$.

An advantage of the present method is that the object is not physically altered during analysis thereof. Thus, the present method is well suited for use as an on-line technique for measuring the density and the mass fractions of the molecular components of soot boules fabricated by the VAD or VRD processes. From a knowledge of the mass fraction of germania in a boule, the mole fraction of germania can easily be determined which can then be used to calculate the refractive index of the boule.

BRIEF DESCRIPTION OF THE DRAWINGS

FIGS. 4 and 5, taken together, illustrate a flow chart representation of a program for computing the attentuation coefficients of the soot boule of FIG. 1.

DETAILED DESCRIPTION

Figure 1:
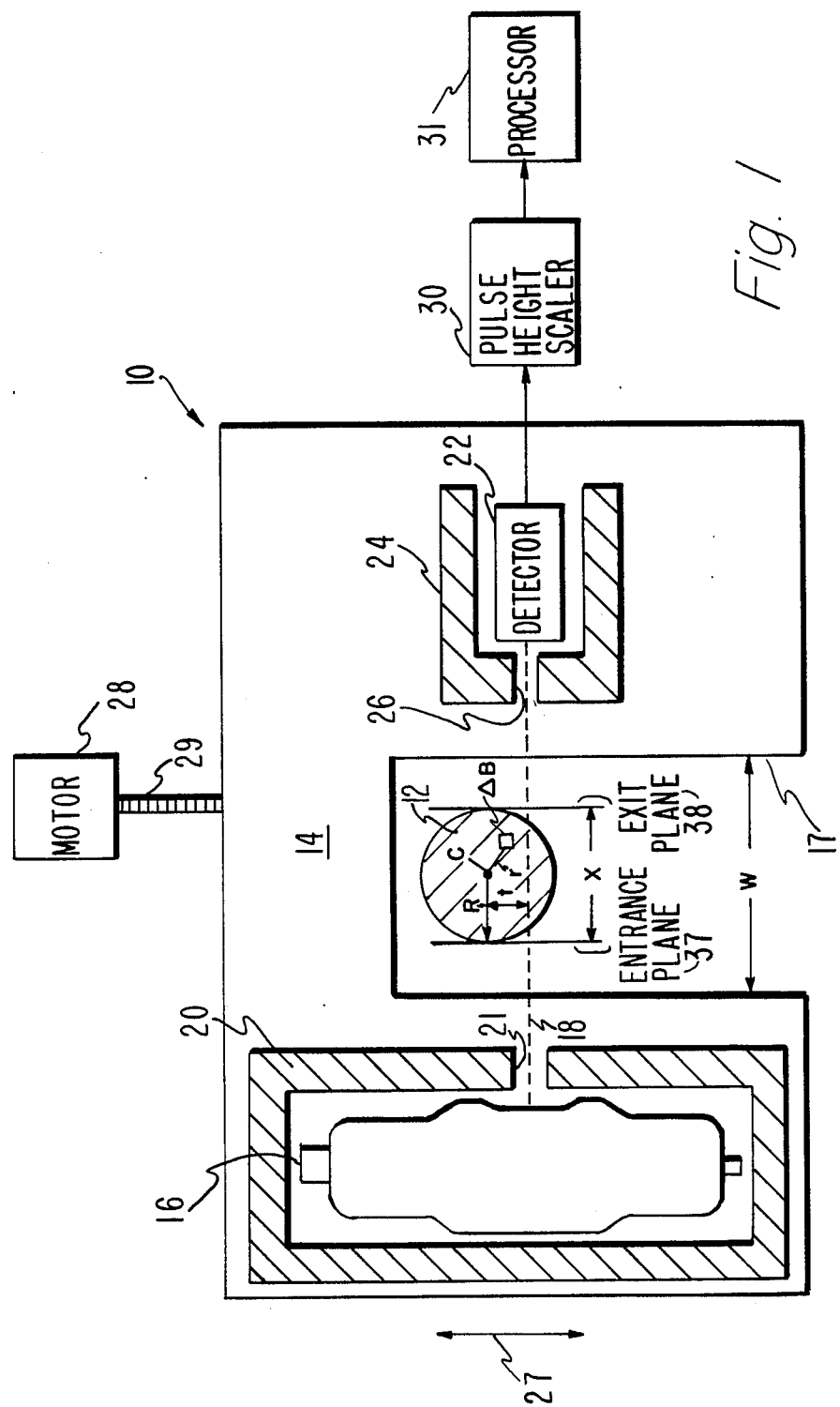
FIG. 1 is a plan schematic view of an apparatus for nondestructively analyzing a soot boule.

FIG. 1 illustrates an apparatus 10 for nondestructively analyzing a generally porous, nonhomogeneous cylindrical object 12 (shown in cross section) such as an unconsolidated soot boule, comprised of n (where n is an integer) known molecular components, to measure the density and each of the n mass fractions thereof. The apparatus 10 comprises a plate 14 upon which is mounted a radiation source 16 on one side of a cutout 17 in the plate. The cutout 17 is sized to receive the boule 12. The radiation source 16 produces a beam 18 comprised of high energy photons, typically in the range of 0 to 120 keV, which bombard the soot boule 12 so as to pass therethrough in a direction perpendicular to the longitudinal axis of the boule.

In practice, the radiation source 16 comprises an x-ray tube, typically a model MCN 161 tube made by Phillips, N.V. of Holland which is excited from a suitable power supply (not shown) which comprises part of a Phillips Model MG 160 X-ray System. As compared to radiation sources which produce photons of a single energy, the x-ray tube 16 possesses a distinct advantage. The beam 18 produced by the tube 16 contains photons each having distinct energy within a continuous spectrum $E_K$ bounded by an upper and lower energy limits, $E_{Khigh}$ and $E_{Klow}$, respectively. The magnitude of the upper energy limit $E_{Khigh}$ depends on the excitation of the x-ray tube 16. Typically, the upper limit $E_{Khigh}$ of the photon energy spectrum is 120 keV. The lower limit $E_{Klow}$ is essentially 0 keV.

In practice, the x-ray tube 16 is housed within a lead shield 20 which is provided with a very small opening 21 facing the cutout 17 in the plate 14 so that the beam 18 produced by the x-ray tube is well collimated. The size of the opening 21 in the shield 20 is typically on the order of 75 microns and has been greatly exaggerated in FIG. 1 for the purposes of illustration. A detector 22 typically a model 905-4 NaI scintillation detector and the circuitry associated with it made by EG&G, Ortec Division, Oakridge, Tenn., is mounted on the plate 14 on the opposite side of the cutout 17 from the x-ray tube 16 so as to be in registration with the beam 18 produced thereby. The detector 22 is housed within a lead shield 24 which has an opening 26 therein directly opposite to, and sized approximately the same as, the opening 21 in the shield 20 surrounding the x-ray tube 16.

The plate 14 is slidably mounted for movement as indicated by the double-ended arrow 27. A motor 28 has its shaft (not shown) coupled to drive a lead screw 29 in threaded engagement with a lead nut (not shown) mounted to the plate 14. As the lead screw 29 is rotatably driven by the motor 28, the plate 14 is displaced in the direction indicated by the arrow 27, causing the beam 18 to be scanned across the boule 12.

A pulse height analyzer/scaler 30, which in practice takes the form of a model 7100 multichannel analyzer made by EG&G Company, Ortec Division, is coupled to the output of the detector 22. The pulse height analyzer determines the energy dependent intensity distribution of the photons in the beam 18. The output pulses of the detector 22 are classified by the analyzer 30 according to their amplitude. In practice, the analyzer 30 is programmed to provide either 512 or 1024 channels (not shown), each channel having a storage register (not shown) associated therewith which is incremented when the amplitude of the output pulse of the detector 22 has the approximate amplitude value established for one of the particular channels. Since the magnitude of each output pulse of the detector 22 is proportional to the energy of the photon of the beam 18 impinging thereon, the analyzer effectively determines the number of the photons in the beam 18 as a function of their energy so as to effectively measure the intensity of the beam. The scaler/analyzer 30 is connected at its output to a processor 31 which takes the form of a digital computer programmed in the manner described hereinafter.

Figure 2:
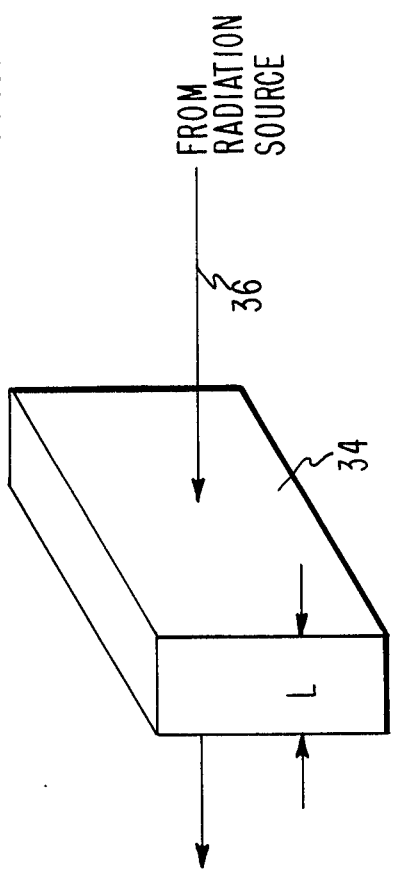
FIG. 2 is a perspective illustration of a slab bombarded by a beam of high energy photons.

In order to fully comprehend the manner by which the apparatus 10 accomplishes nondestructive analysis of the boule 12, a brief discussion of the way in which a beam of high energy photons is attenuated upon the passage thereof through matter may be helpful. Referring to FIG. 2, there is shown a homogeneous slab 34 of a monoatomic material comprised of an atomic species i. The slab 34, which is of a thickness L, is bombarded by a beam 36 comprised of photons, each having the same energy E. As the beam 36 propagates through the slab 34, the intensity thereof is attenuated exponentially. Mathematically, the attenuation of the intensity of the beam 36 propagating through the slab 34 is given by the relationship $$I(E,L) = I(E,O)^{-\mu_i(E)L} \tag{1}$$

where $I(E,O)$ and $I(E,L)$ are the intensities of the beam upon entering and exiting the slab, respectively, and $\mu_i(E)$ is the attenuation coefficient of the slab.

The attenuation coefficient $\mu_i(E)$ for the slab 34, when bombarded by the beam 36 comprised of photons of energy E, is given by $$\mu_i(E) = \frac{N_a \left[\frac{atoms}{mole}\right]}{A_i \left[\frac{g}{mole}\right]} \rho_i \left[\frac{g}{cm^3}\right] \sum_{j=1}^{n} \sigma_j^{(i)}(E) \left[\frac{cm^2}{atom}\right] \tag{2}$$

where $N_a$ is Avogadro's number, $A_i$ is the atomic weight of the atoms of the species i comprising the slab, $\rho_i$ is the density of the slab and $\sigma_j^{(i)}(E)$ is the probability or atomic cross section of a photon of energy (E) being removed by the interaction process j with an atom of the species i.

The attenuation of the beam 36 is not only dependent on the photon energy E thereof, but also upon the atomic species i of the slab 34 through which the beam propagates, as indicated by the use of the subscript and superscript i in equation (2). Certain atomic species are more efficient absorbers of high energy photons than others. For example, germanium is a much better absorber of high energy photons than silicon which in turn is a much better absorber than air. It is this very phenomena which is exploited by the apparatus 10 of FIG. 1 to measure the density and the mass fraction of each of the n molecular components of the soot boule 12.

Not only is the attenuation of the beam 36 of FIG. 2 dependent upon the atomic species i comprising the slab 34, but also, the physical state of the slab affects the attenuation of the beam. The dependence of the attenuation of the beam 36 on the physical state of the slab 34 can be eliminated by dividing equation (2) by the density $\rho_i$ of the slab. The term $\mu_i/\rho_i$ is referred to as the mass attenuation coefficient.

The mass attenuation coefficient for a composite material comprised of n atomic components each of a species i is given by the sum of each individual product of the mass attenuation coefficient for each atomic species $\mu_i(E)/\rho_i$ and the mass fraction $x_i$ thereof. Mathematically, this can be expressed by the relationship $$\frac{\mu(E)}{\rho} = \sum_{i=1}^{n} \frac{\mu_i(E)}{\rho_i} x_i \quad (3)$$

where the term $\mu(E)/\rho$ on the left-hand side of equation (3) represents the mass attenuation coefficient of the composite material. The subscript i on the right-hand side of equation (3) need not denote a particular atomic species but can also refer to a molecular species, such as germanium dioxide, silicon dioxide or air which is a bulk absorber of photons. When the subscript i refers to a molecular species, then the term $\mu_i(E)/\rho_i$ refers to the mass attenuation coefficient of the particular molecular species i.

Referring back to FIG. 1, the unconsolidated boule 12 is usually comprised of three molecular components—air, amorphous silicon dioxide ($SiO_2$) and amorphous germanium dioxide ($GeO_2$), in decreasing order of concentration. With this knowledge, equation (3) can be specifically written for the soot boule 12 as follows $$\frac{\mu(r, E)}{\rho(r)} = \frac{\mu_{SiO_2}(E)}{\rho_{SiO_2}} x_{SiO_2}(r) + \frac{\mu_{GeO_2}(E)}{\rho_{GeO_2}} x_{GeO_2}(r) + \frac{\mu_{air}(E)}{\rho_{air}} x_{air}(r) \quad (4)$$

the terms $\rho_{SiO_2}$, $\rho_{GeO_2}$ and $\rho_{air}$ represent the individual densities of silicon dioxide, germanium dioxide and air, respectively, which can be readily obtained from a suitable reference text. The terms $\mu_{SiO_2}(E)$, $\mu_{GeO_2}(E)$ and $\mu_{air}(E)$ represent the linear attenuation coefficients for silicon dioxide, germanium dioxide and air, respectively. These quantities can be determined by means of a suitable calibration procedure described later. Note that since the boule 12 is inhomogeneous, the mass attenuation coefficient thereof is radially dependent so that density and each of the molecular mass fractions of the boule obtained from equation (4) will also be radially dependent.

Equation (4) is only valid when the photons bombarding the composite material are of a single energy E. However, as indicated previously, the beam 18 produced by the x-ray source 16 has a continuous energy spectrum $E_K$. To account for the polychromatic nature of the beam 18, equation (4) must be modified as follows $$\frac{\bar{\mu}(r,E_K)}{\rho(r)} = \frac{\bar{\mu}_{SiO_2}(E_K)}{\rho_{SiO_2}} X_{SiO_2}(r) + \frac{\bar{\mu}_{GeO_2}(E_K)}{\rho_{SiO_2}} X_{GeO_2}(r) + \frac{\bar{\mu}_{air}(E_K)}{\rho_{air}} X_{air}(r) \quad (5)$$

where the term $\bar{\mu}(r,E_K)$ is given by $$\bar{\mu}(r,E_K) = \int_{E_{Klow}}^{E_{Khigh}} \mu(r,E) dE \quad (6)$$

where $E_{Khigh}$ and $E_{Klow}$ represent the upper and lower energy bounds of the spectrum $E_K$. The terms $\bar{\mu}_{SiO_2}(E_K)$, $\bar{\mu}_{GeO_2}(E_K)$ and $\bar{\mu}_{air}(E_K)$ are given by equations (7), (8) and (9), respectively.

$$\bar{\mu}_{SiO_2}(E_K) = \int_{E_{Klow}}^{E_{Khigh}} \mu_{SiO_2}(E) dE \quad (7)$$

$$\bar{\mu}_{GeO_2}(E_K) = \int_{E_{Klow}}^{E_{Khigh}} \mu_{GeO_2}(E) dE \quad (8)$$

$$\bar{\mu}_{air}(E_K) = \int_{E_{Klow}}^{E_{Khigh}} \mu_{air}(E) dE \quad (9)$$

Determining the attenuation coefficient of a round, inhomogeneous object, such as the soot boule 12 of FIG. 1, is not as straightforward as determining the attenuation coefficient for the homogeneous slab 34 of FIG. 2. The attenuation coefficient of the slab 34 is easily determined from equation (1) by measuring the intensity of the beam upon entering and exiting the slab and the thickness L thereof. However, the attenuation coefficient of the boule 12 is dependent on its radius as well as the energy of the incident beam and thus, a more involved procedure is associated with its calculation.

Referring back to FIG. 1, the attenuation coefficient of the boule 12 can be determined in accordance with the attenuation of the beam 18 propagating therethrough. Such a determination can be facilitated by recognizing that the detector 22 actually senses the intensity of the beam 18 upon the propagation thereof between an entrance plane 37 and an exit plane 38 which are each parallel to the other and are each tangent to the boule 12 on opposite sides thereof.

If one temporarily assumes that the beam 18 is monochromatic, that is, each photon thereof has an energy E, then the intensity thereof exiting the plane 38 is given by $$i(E,t) = i_o(E) \exp\left[ -2\mu_{air}(R - \sqrt{R^2 - t^2}) - \int_{L(t)} \mu(r,E) dx \right] \quad (10)$$

for the condition where the height t of the beam, that is the distance of the axis thereof from the center c of the boule 12, is less than the boule radius R. When the height t of the beam 18 is greater than the radius R of the boule 12, the intensity of the beam is given by the expression $$i(E,t>R) = i_o(E) \exp[-2\mu_{air}R] \quad (11)$$

As indicated by equation (11), air is an absorber of the beam 18, albeit a weak one. Thus, the intensity of the beam 18 is attenuated during the propagation thereof through space outside of the region between the entrance and exit planes 37 and 38, respectively. However, the attenuation of the intensity of the beam 18 suffered upon the propagation thereof through space outside of the region between the entrance and exit planes 37 and 38, respectively, is of little concern. The detector 22 effectively only measures the increased attenuation of the intensity of the beam 18 upon the propagation thereof inside the boule 12.

The term L(t) in equation (10) represents the path over which the beam 18 suffers attenuation inside the boule 12. By changing the variable integration from x, which represents the linear path between the entrance and exit planes 37 and 38, respectively, to r, which represents the distance along the radius R of the boule 12, the term $\int_{L(t)} \mu(r,E) dx$ can be expressed as $$\int_{L(t)} \mu(r,E) dx = 2 \int_t^R \frac{\mu(r,E) r}{(r^2 - t^2)^{\frac{1}{2}}} dr \qquad (12)$$

The ratio of the intensity of the beam 18 at the exit plane 38 for the condition $t < R$ to the intensity of the beam for the condition $t > R$ can be obtained by dividing equation (10) by equation (11). Taking the logarithm of the resulting equation and integrating the right-hand side by parts, one obtains $$\log\left[\frac{i(E,t)}{i(E,t > R)}\right] = \qquad (13)$$

$$2 \int_t^R (r^2 - t^2)^{\frac{1}{2}} \frac{d}{dr} [\mu(r,E) - \mu_{air}(E)] dr$$

where the term $\mu(r) = \mu_{air}$ for the condition $t > r$.

By differentiating equation (13) with respect to t and subsequently inverting the resultant integral, the attenuation coefficient $\mu(r,E)$ can be expressed as $$\mu(r,E) - \mu_{air}(E) = \qquad (14)$$

$$\frac{1}{\pi} \int_r^R \frac{d}{dt}\left[\log\frac{i(E,t)}{i(E,t > R)}\right] \frac{dt}{(t^2 - r^2)^{\frac{1}{2}}}$$

From equation (14), the linear attenuation coefficient $\mu(r,E)$ can be determined in accordance with the measured ratio of the beam intensities $i(E,t)/i(E,t>R)$.

Equation (14) is valid only when the beam 18 passing through the boule 12 is assumed to be monochromatic. However, the beam 18 produced by the x-ray tube 12 is polychromatic so that equation (12) must be modified as follows $$\bar{\mu}(r) - \bar{\mu}_{air} = \frac{1}{\pi} \int_r^R \frac{d}{dt} f(t) \frac{dt}{(t^2 - r^2)^{\frac{1}{2}}} \qquad (15)$$

where the term f(t) is given by $$f(t) = \int_{E_{Klow}}^{E_{Khigh}} \log\left[\frac{i(E_K, t)}{i(E_K, t > R)}\right] dE \qquad (16)$$

The ratio $i(E,t)/i(E,t>R)$ in equation (16) is the ratio of the intensity of those photons of the beam 18 which have energies within an incremental range $\Delta E$ about an energy E within the bounds of the energy spectrum $E_K$. Such a ratio is given by the count of photons associated with each separate one of the channels of the analyzer 30. The quantity f(t) in equation 16, which is characteristic of all the photons in the beam, is obtained by integrating the logarithm of the intensity ratio $i(E,t)/i(E,t>r)$ of photons of any particular energy E within the energy limits of the beam 18. When the beam 18 is polychromatic, then a statement indicating that the attenuation coefficient $\mu(r)$ for photons within a certain energy group is established in accordance with the ratio of the intensity of photons leaving the boule to those entering the boule implies that the coefficient is calculated in accordance with equations (15) and (16). For a monochromatic beam of photons such a statement implies that coefficient is calculated in accordance with equation (14).

Once the attenuation coefficient of the boule 12 has been determined from equations (15) and (16) for the polychromatic beam 18, then equation (5) can be used to provide an expression characterizing the boule parameters $\rho(r)$, $X_{SiO2}(r)$, $X_{GeO2}(r)$ and $X_{air}(r)$ in terms of known quantities. However, since there are four unknown parameters, four equations relating these unknowns are necessary in order to find a unique solution therefor.

The law of conservation of mass may be utilized to generate two additional equations relating the unknown parameters of the boule 12 to known quantities. For a small volume element $\Delta B$ of the boule 12 located a distance r from the center c thereof, the sum of the mass fractions of the constituents $X_{SiO2}(r)$, $X_{GeO2}(r)$ and $x_{air}(r)$ of the boule must equal unity. Mathematically, this may be expressed as $$X_{SiO2}(r) + x_{GeO2}(r) + x_{air}(r) = 1 \qquad (17)$$

The partial volume of the individual constituents in the volume element $\Delta B$ may be summed to yield the total volume of the element $\Delta B$. Mathematically, this may be expressed by the relationship $$\frac{x_{SiO2}}{\rho_{SiO2}} + \frac{x_{GeO2}}{\rho_{GeO2}} + \frac{x_{air}}{\rho_{air}} = \frac{1}{\rho(r)} \qquad (18)$$

A fourth equation relating the individual components of the boule 12 may be obtained by measuring the linear attenuation coefficient $\mu(r,E)$ thereof for photons within a second energy group, thereby yielding an additional equation of the same form as equation (5) but with different coefficients. The four equations may be written in a matrix equation $$\begin{pmatrix} \frac{\bar{\mu}_{SiO2}(E_a)}{\rho_{SiO2}} & \frac{\bar{\mu}_{GeO2}(E_a)}{\rho_{GeO2}} & \frac{\bar{\mu}_{air}(E_a)}{\rho_{air}} & -\bar{\mu}(r, E_a) \\ \frac{\bar{\mu}_{SiO2}(E_b)}{\rho_{SiO2}} & \frac{\bar{\mu}_{GeO2}(E_b)}{\rho_{GeO2}} & \frac{\bar{\mu}_{air}(E_b)}{\rho_{air}} & -\bar{\mu}(r, E_b) \\ 1 & 1 & 1 & 0 \\ \frac{1}{\rho_{SiO2}} & \frac{1}{\rho_{GeO2}} & \frac{1}{\rho_{air}} & -1 \end{pmatrix} \begin{pmatrix} x_{SiO2}(r) \\ x_{GeO2}(r) \\ x_{air}(r) \\ \frac{1}{\rho(r)} \end{pmatrix} = \qquad (19)$$

$$\begin{pmatrix} 0 \\ 0 \\ 1 \\ 0 \end{pmatrix}$$

The arguments $E_a$ and $E_b$ of the attenuation coefficients in the first and second lines of equation (19) denote that the coefficients are valid for photons within each of two different energy groups $E_a$ and $E_b$, respectively, within the spectrum $E_K$ of the beam 18. Each of the energy groups $E_a$ and $E_b$ within the energy spectra $E_K$ has an upper and lower energy bound $E_{high}$ and $E_{low}$, respectively. By inverting equation (19), the column vector comprising the four unknown parameters can be obtained, thus providing a solution to the problem.

From a knowledge of the individual mass fractions $X_{SiO_2}(r)$, $X_{GeO_2}(r)$ and $X_{air}(r)$, the mole fraction of germanium in the boule 12 can be computed. The mole fraction of germanium in the boule 12 is a useful quantity because the refractive index of the boule has been found to be proportional thereto.

Figure 3:
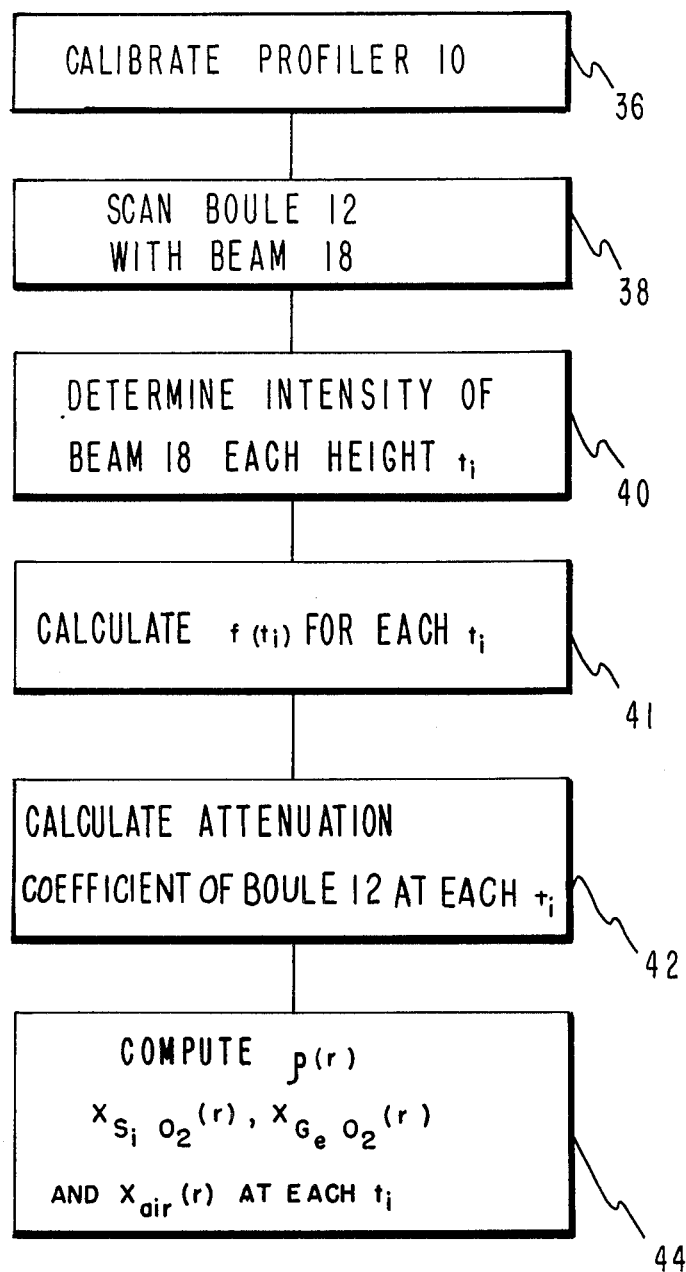
FIG. 3 is a table generally depicting the steps of the measurement method of the present invention.

FIG. 3 is a block diagram depicting the individual steps associated with determining the density $\rho(r)$ and each of the mass fractions $X_{SiO_2}(r)$, $X_{GeO_2}(r)$ and $X_{air}(r)$ of the constituents of the boule 12. Initially, the apparatus 10 of FIG. 1 is calibrated (step 36) so as to determine the actual values for $\mu_{air}(E)$, $\mu_{SiO_2}(E)$ and $\mu_{GeO_2}(E)$ for the photons within the two energy groups $E_a$ and $E_b$. Determination of the actual values of the attenuation coefficient of air, $SiO_2$ and $GeO_2$ is accomplished by directing the beam 18 through samples (not shown) of air, $SiO_2$ and $GeO_2$, respectively. The intensity of the photons in each of the energy groups $E_a$ and $E_b$ within the spectrum $E_K$ of beam 18 entering and leaving each sample, as well as the width of each sample, are measured. From this data, the attenuation coefficient of air, $SiO_2$ and $GeO_2$ can be calculated from equation (1) and equations (7), (8) and (9), respectively.

It is only necessary to calibrate the apparatus 10 of FIG. 1 once as long as each boule 12 profiled thereby is comprised of air, amorphous silicon dioxide and amorphous germanium dioxide. However, if there are additional constituent compounds in the boule 12, then the apparatus 10 must be recalibrated so as to determine the linear attenuation coefficient of each additional constituent for photons in each energy group.

After the apparatus 10 has been calibrated, then the boule 12 is positioned in the cutout 17 (FIG. 1) of the plate 14 (FIG. 1) and is subsequently scanned by beam 18 (step 38 of FIG. 3). As described, scanning of the boule 12 by the beam 18 is accomplished by moving the plate 14 in the direction of the double-ended arrow 27. Alternatively, the plate 14 could be kept stationary while the boule 12 was moved across the beam 18.

As the boule 12 is scanned, the intensity spectrum of the beam 18 at the exit plane 38 in FIG. 1 is recorded at each of a plurality of discrete heights $t_i$ (step 40). In practice, the intensity spectrum of the beam 18 is determined at each of 400 separate heights (i=400), each 0.01 cm apart during movement of the plate 14 in the direction indicated by the double-ended arrow 27.

As discussed previously, in order to solve equation (19) to obtain values for the density $\rho(r)$ and the individual mass fractions $X_{SiO_2}(r)$, $X_{GeO_2}(r)$ and $X_{air}(r)$ of the boule 12, the attenuation of the intensity of the beam 18 at each height $t_i$ must be obtained by measuring the attenuation of the photons with energies within each of two different energy groups $E_a$ and $E_b$. Each of these energy groups may comprise more than one of the channels of the analyzer 30. As discussed previously, the beam 18 is polychromatic, that is to say, it contains photons of varying energy levels between $E_{Khigh}$ and $E_{Klow}$. By measuring the attenuation of photons in each of two distinct energy groups $E_a$ and $E_b$ within the overall energy spectrum $E_K$ of beam 18, the boule 12 need only be scanned once. The pulse height scaler/analyzer 30 can readily be adjusted to count the number of photons propagating through the boule 12 which have an energy level within one of the two energy groups $E_a$ and $E_b$ within the energy spectra $E_K$ of the beam 18. From the data provided by the pulse height analyzer 30, two separate attenuation coefficients for the boule 12 can be obtained in accordance with equations (15) and (16) by substituting the upper and lower energy limits $E_{High}$ and $E_{Low}$ of each of energy group $E_a$ and $E_b$ for the upper and lower limits $E_{Khigh}$ and $E_{Klow}$ of the energy spectra $E_K$ of the beam 18.

Once the intensity of the beam 18 is measured in the above-described manner at each height $t_i$, then a data value $f(t_i)$, representing the ratio of attenuated intensity of the beam to the incident intensity thereof for the photons within each of the two energy groups $E_a$ and $E_b$ is calculated (step 41). Mathematically, the data value $f(t_i)$ is determined in accordance with equation (20).

$$f(t_i) = \int_{E_2}^{E_1} \log\left(\frac{i(E, t_i)}{i(E, t > R)}\right) dE \tag{20}$$

The particular values of the upper and lower energy boundary limits $E_1$ and $E_2$ in equation (20) correspond to the energy limits $E_{High}$ and $E_{Low}$ for the energy groups $E_a$ and $E_b$.

Following step 41, a pair of linear attenuation coefficients $\bar{\mu}(r,E_a)$, $\bar{\mu}(r,E_b)$ for the boule 12 are computed at each height $t_i$ of the beam 18 for the photons within each of the two energy groups $E_a$ and $E_b$ (step 42). Calculation of the attenuation coefficients is accomplished by the computer 31 of FIG. 1 upon executing a program which is further described with respect to FIG. 4 four times, twice for each half of the boule 12. Once the two attenuation coefficients of the boule 12 have been calculated, then the density $\rho(r)$ and the mass fractions $x_{air}(r)$, $x_{SiO_2}(r)$ and $x_{GeO_2}(r)$ can be determined by solving equation (19) (step 44).

Figure 4:
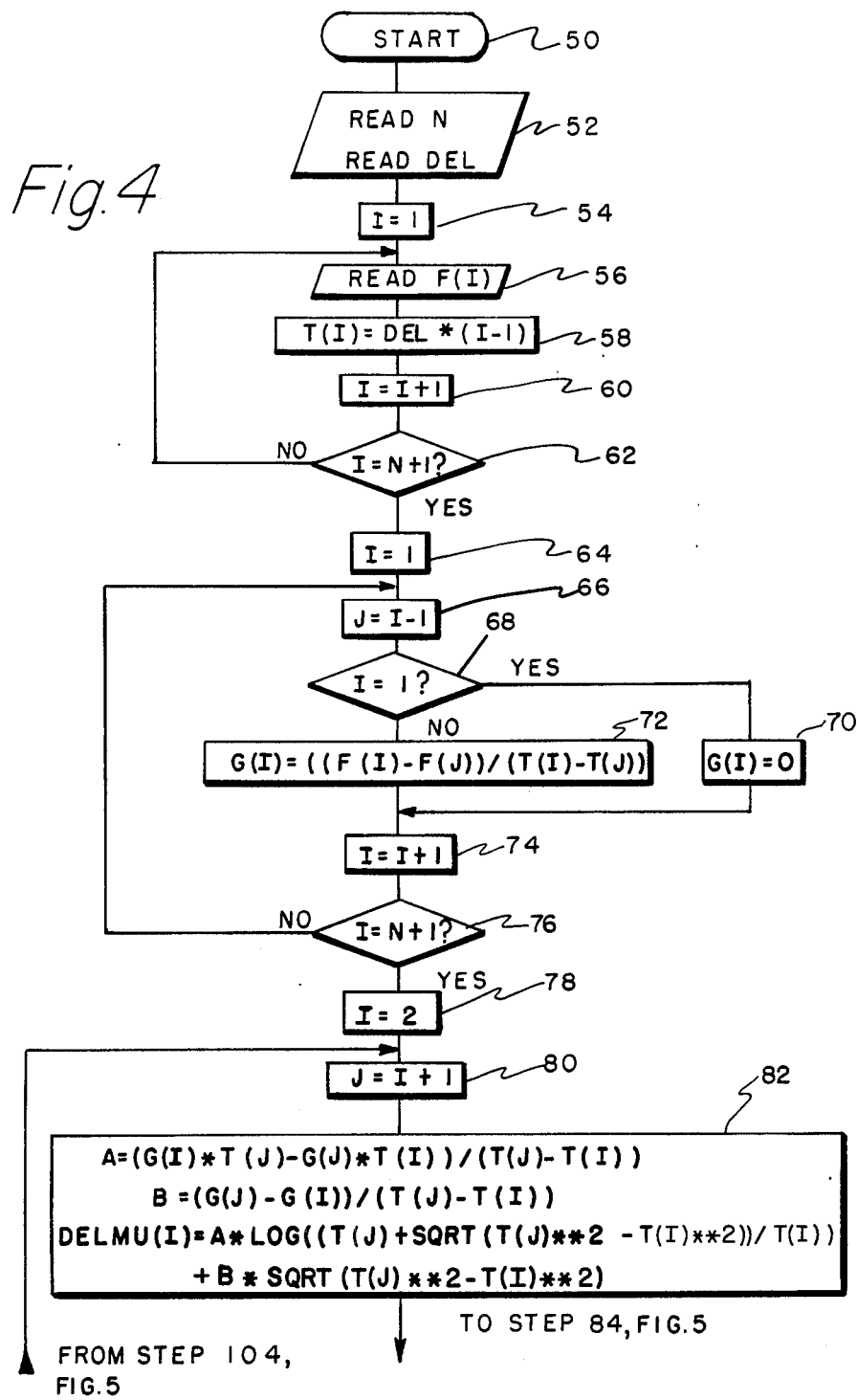

FIGS. 4 and 5, taken together, depict a flow chart representation of the program executed by the computer 31 of FIG. 1 to numerically solve equation (15) to determine each of the attenuation coefficients $\bar{\mu}(r,E_a)$ and $\bar{\mu}(r,E_b)$ of the boule 12 for the photons in each of the energy groups $E_a$ and $E_b$ of the beam 18 at each height $t_i$ thereof. Referring to FIG. 4, upon commencement of the program, the start step (step 50) is executed by the computer 31 to clear scratch pad memory locations therein which may not have been cleared previously. Thereafter, a numerical value for each of a pair of variables N and DEL is read from a memory location in the computer 31 (step 52). The variable N represents the number of intervals at which the intensity of the beam 18 is measured. In other words, the variable N corresponds to the number of discrete heights $t_i$ of the beam 18 for one half of the boule 12. The variable DEL represents the spacing between successive heights $t_i$ of the beam 18. Typically, N and DEL are assigned the values 200 and 0.01, respectively.

Next, a variable I is set initially equal to 1 (step 54). Thereafter, a stored data value, representing the Ith component of a vector quantity F(I), whose components each correspond to a separate one of the i values of $f(t_i)$ determined during step 38 of FIG. 3 for photons of the beam 18 within one of the two energy groups $E_a$ and $E_b$, is read from a memory location in computer 31 (step 56). Following step 56, the Ith component of a vector quantity T(I) is established in accordance with equation $$T(I) = DEL*(I-1) \tag{21}$$

(step 58).

Thereafter, the value of I is augmented by 1 (step 60). The newly augmented value of I is then compared to the value of the quantity N+1 (step 62). For so long as the value of I does not exceed the value of the quantity N+1, then program execution branches back to step 56 and those following it to read in each of the N components of the vector F(I) and to compute the N separate components of the vector quantity T(I).

Once the value of I equals the value of the quantity N+1 then step 64 is executed whereupon the value of I is reset to 1. Next, a variable J is set equal to the quantity I−1 (step 66). The value of I is then tested (step 68) to see whether or not the current value thereof equals unity. Should the value of I be equal to 1, as will occur upon the initial execution of step 68, then the program execution branches to step 70 whereupon a vector quantity G(I), whose individual components each represent a separate one of the i values of the term df($t_i$)/dt, has the first component thereof set equal to zero to account for the fact that value of $$\frac{d}{dt} \log \frac{i(E, t = 0)}{i(E, t > R)} = 0$$

If, upon execution of step 68, the value of I is found not to be equal to 1, then the Ith component of the vector of G(I) is calculated (step 72) in accordance with equation $$G(I) = ((F(I) - F(J))/(T(I) - T(J))) \quad (22)$$

Those skilled in the art will recognize that the value assigned to the Ith component of the G(I) during step 72 is a numerical approximation of the value of the term df($t_i$)/dt.

Following either steps 70 or 72, the value of I is incremented by 1 (step 74). Thereafter, the newly augmented value of I is compared to the value of the quantity N+1 (step 76). For so long as the value of I is less than the value of the quantity N+1, then program execution branches back to step 66 and those following it to calculate the value for each of the N components of the vector G(I).

Should the current value of the variable I equal the value of quantity N+1, indicating that the N components of the vector G(I) have been calculated, then the computer 31 proceeds to numerically calculate an integral of the form $$\int_{t_i}^{t_N} \frac{g(t)dt}{(t^2 - t_i^2)^{\frac{1}{2}}} = \sum_{j=i}^{N-1} \int_{t_j}^{t_{j+1}} \frac{g(t)dt}{(t^2 - t_i^2)^{\frac{1}{2}}} \quad (23)$$

which corresponds to the integral of equation (15), using the trapezoidal rule.

In order to better understand the steps executed by the computer 31 to accomplish numerical calculation of the integral, some background discussion may prove helpful. The trapezoidal rule provides that an integral can be approximated by the sum of the individual discrete area elements under the curve thereof. Applying the trapezoidal rule to the integral on the left-hand side of equation (23), one obtains $$\int_{t_i}^{t_N} \frac{g(t)dt}{(t^2 - t_i^2)^{\frac{1}{2}}} \approx \int_{t_i}^{t_{i+1}} \frac{g(t)dt}{(t^2 - t_i^2)^{\frac{1}{2}}} + \quad (24)$$

$$\sum_{j=i+1}^{N-1} \left[ \frac{g(t_j)}{(t_j^2 - t_i^2)^{\frac{1}{2}}} + \frac{g(t_{j+1})}{(t_{j+1}^2 - t_i^2)^{\frac{1}{2}}} \right] (t_{j+1} - t_j)/2$$

where $t_i$ represents the Ith value of the height of the beam 18. Note that the first partial integral in equation (23) cannot be approximated by a trapezoidal area element since the term $$\frac{g(t_j)}{(t_j^2 - t_i^2)^{\frac{1}{2}}}$$

becomes infinite for j=i.

In order to numerically calculate the integral on the right-hand side of equation (24), it is necessary to approximate the term g(t) by $$g(t) = g(t_i) + \frac{g(t_{i+1}) - g(t_i)}{(t_{i+1} - t_i)} (t - t_i) = A + Bt \quad (25)$$

for $t_i < t < t_{i+1}$. The constants A and B in equation (25) are given by $$A = \frac{g(t_i)t_{i+1} - g(t_{i+1})t_i}{t_{i+1} - t_i} \quad (26)$$

and $$B = \frac{g(t_{i+1}) \cdot g(t_i)}{t_{i+1} - t_i} \quad (27)$$

Substituting g(t) as given by equation (25) into the integral on the right-hand side of equation (24), one obtains an integral given as $$\int_{t_i}^{t_{i+1}} \frac{(A + Bt)dt}{(t^2 - t_i^2)^{\frac{1}{2}}}$$

which can be evaluated analytically with the solution being $$A \log \left[ \frac{t_{i+1} + (t_{i+1}^2 - t_i^2)^{\frac{1}{2}}}{t_i} \right] + B(t_{i+1}^2 - t_i^2)^{\frac{1}{2}}$$

Substituting this solution for the integral on the right-hand side of equation (24) one arrives at $$\int_{t_i}^{t_N} \frac{g(t)dt}{(t^2 - t_i^2)^{\frac{1}{2}}} = \quad (28)$$

$$A \log \left[ \frac{t_{i+1} + (t_{i+1}^2 - t_i^2)^{\frac{1}{2}}}{t_i} \right] + B(t_{i+1}^2 - t_i^2)^{\frac{1}{2}} +$$

$$\sum_{j=i+1}^{N-1} \left[ \frac{g(t_j)}{(t_j^2 - t_i^2)^{\frac{1}{2}}} + \frac{g(t_{j+1})}{(t_{j+1}^2 - t_i^2)^{\frac{1}{2}}} \right] (t_{j+1} - t_j)/2$$

where A and B are given by equations (26) and (27), respectively. Thus, equation 28 allows the integral in equation (23) to be calculated from the data previously computed during step 72.

In order to solve for the integral $$\int_{t_i}^{t_N} \frac{g(t)dt}{(t^2 - t_i^2)^{\frac{1}{2}}}$$

in the manner set forth above, after step 76, the variable I is assigned the value of 2 (step 78) and the variable J is assigned the value of the quantity I+1 (step 80). Following step 80, step 82 is executed whereupon values for each of a pair of variables A and B are determined in accordance with equations (31) and (32)

$$A = (G(I)*T(J) - G(J)*T(I))/(T(J) - T(I)) \tag{31}$$

$$B = (G(J) - G(I))/(T(J) - T(I)). \tag{32}$$

As may be appreciated, the variables A and B in equations (31) and (32) represent numerical values of the arguments A and B, respectively, in equations (24) and (25), respectively, described earlier.

Also during step 82, a vector quantity DELMU(I) has its Ith component assigned a value in accordance with the equation (32)

$$DELMU(I) = A *$$
$$LOG((T(J) + SQRT(T(J)2 - T(I)2))/T(I)) + B$$
$$* SQRT(T(J)2 - T(I)2) \tag{33}$$

As may be appreciated upon a comparison of equation (33) to equation (28), the Ith component of the vector DELMU(I) is a numeric approximation of the value of the first two terms of the left-hand side of equation (28) for the Ith value of the height $t_i$ of the beam 18.

Following step 82 of FIG. 4, the value of the variable I is then tested to determine whether or not the magnitude thereof is greater than the value of the quantity N−1 during step 84 shown in FIG. 5. Should the value of I be less than the value of the quantity N−1 indicating that the computer 31 has yet to complete calculation of the N separate components of the vector DELMU(I), then the variable J is assigned the value of the quantity I+1 (step 86) and thereafter, a variable D is assigned the value 1.0 (step 87).

Next, the value of the variable J is tested (step 88) by comparison thereof to the value of both the quantities I+1 and N. When the value of J is equal to the value of either the quantities I+1 or N, then, the variable D is reassigned the value 0.5 (step 90) before proceeding to step 92. Otherwise, when the value of J is unequal to the value of either of the quantities I+1 or N, program execution branches directly from step 88 to 92, omitting the execution of step 90.

Upon the execution of step 92, the value of the expression $G(J)*(T(J) - T(I))*D/\sqrt{T(J))^2 - (T(I))^2}$ is added to the Ith component of the vector DELMU(I). Augmenting the Ith component of the vector DELMU(I) by this expression achieves a numerical approximation of the sum of the succeeding terms in equation (28) following the first two terms thereof. Since each component of the vector DELMU(I) is to represent the sum of the terms in equation (23) for the Ith value of the height $t_i$ of the beam 18 of FIG. 1, it is necessary to adjust the value of the variable D, as was accomplished during the step 90, to account for the factor of ½ found in that equation.

Following step 92, the value of the variable J is augmented by 1 (step 94) before comparing the current value of that variable to the value of the quantity N+1 (step 96). Should the value of J not equal the value of the quantity N+1, then program execution branches back to step 87 and those following it to accomplish a numerical approximation of the sum of all of the terms of equation (24).

Should the value of J be greater than the value quantity N+1 then, following step 96, program execution branches to step 98 whereupon the Ith component of the vector DELMU(I) is attenuated by $1/\pi$ (step 98). Attenuating the value of the Ith component of the vector DELMU(I) during step 98 insures that the term $1/\pi$ which is present in equation (15) is accounted for. The execution of step 98 also follows the execution of step 84 when the value of I equals the value of the quantity N−1 which occurs when all but the Nth component of the vector DELMU(I) has been calculated.

Following step 98, the Ith component of the vector DELMU(I) is then written into a memory location (not shown) within the computer 31 (step 100) Next, the value of the variable I is augmented by 1 (step 102). Thereafter, the value of the variable I is compared to the value of the quantity N−1 (step 104). If, during step 104, the value of I is unequal to the quantity N−1, then program execution branches back to step 80 and those following it so that all but the Nth component of the variable DELMU(I) are calculated.

Otherwise, when the value of I equals the quantity N−1, then after step 104, program execution branches to step 106 whereupon the Nth component of the vector DELMU(I) is set equal to 0 to account for the fact that, when the height $t_i$ of the beam 18 equals the radius R of the boule 12 of FIG. 1, the linear attenuation coefficient at that height is zero. Following step 106, the value of the Nth component of the vector DELMU(I) is written into a memory location in computer 31 (step 108) before program execution stops (step 110).

The above-described program is executed four times. The first two times, the program calculates the attenuation coefficient for each half of the boule 12 at each height $t_i$ for photons with energies within the group $E_a$. Upon the third and fourth execution of the program, the attenuation coefficients for each half of the boule 12 at each height $t_i$ for photons with energies within the second group $E_b$ is determined.

The apparatus 10 of FIG. 1 can analyze inhomogeneous cylindrical objects such as soot boules having as many as n molecular components, provided that the scaler/analyzer 30 has at least n−1 channels and is capable of resolving the energy level of the photons of the beam 18 striking the detector 22 into one of n−1 discrete energy groups. From the data provided by the scaler/analyzer 30, the computer 31 can, by executing the program of FIG. 4 two times n−1 times, determine each of the n−1 attenuation coefficients of the object for the photons in each of the n−1 energy groups. Once the n−1 attenuation coefficients have been calculated, then the computer 31 can determine each of the mass fractions $X_1(r), X_2(r), \ldots X_n(r)$ and the density $\rho(r)$ of the object using techniques similar to that used to solve equation (19).

It is to be understood that the various embodiments described herein are merely illustrative of the principles of the invention. Various modifications may be made thereto by persons skilled in the art which may embody the principles of the invention and fall within the spirit and scope thereof.

What is claimed is:

1. A method for nondestructively analyzing a porous, inhomogeneous, generally cylindrical object having n known molecular components (where n is an integer) to determine the density and the mass fractions of each of the n molecular components thereof comprising the steps of:

scanning the object with a beam of photons whose axis is perpendicular to the longitudinal axis of the object, each photon having a distinct at least one of $n-1$ energy groups;

measuring the intensity of the photons in each energy group upon the passage of the beam through the object at each of a plurality of separate heights $t_i$ of the beam as measured from the axis thereof to the center of the object;

establishing each of $n-1$ attenuation coefficients $\mu_1(r), \mu_2(r) \ldots \mu_{n-1}(r)$ for the object at each height $t_i$ of the beam thereof in accordance with the measured intensity of the photons within a separate one of the $n-1$ energy groups, respectively; and calculating the density $\rho(r)$ and the mass fraction of each of the n molecular components of the object at said each height $t_i$ of the beam thereof in accordance with each of the $n-1$ attenuation coefficients $\mu_1(r), \mu_2(r) \ldots \mu_{n-1}(r)$.

2. The invention according to claim 1 wherein the object is scanned by bombarding the object with an x-ray beam.

3. The invention according to claim 1 wherein each of the $n-1$ attenuation coefficients is established from the ratio of the intensity of the photons with a respective one of the $n-1$ energy groups leaving the object to the intensity thereof entering the object.

4. The method according to claim 1 wherein the cylindrical inhomogeneous object is a soot boule comprised of air, amorphous silicon dioxide and amorphous germanium dioxide.

5. An apparatus for nondestructively analyzing a porous, inhomogeneous object having n known molecular components (where n is an integer) comprising:

means for scanning the object with a beam of photons whose axis is perpendicular to the axis of the object, each photon having a distinct energy within at least one of $n-1$ energy groups;

means for measuring intensity of the photons upon passage through the object at each of a plurality of separate heights $t_i$ of the beam as measured between the axis thereof and the center of the object;

means for establishing $n-1$ attenuation coefficients $\mu_1(r), \mu_2(r) \ldots \mu_{n-1}(r)$ at each said height $t_i$ of the beam in accordance with the measured intensity of the photons within a separate one of said $n-1$ energy groups, respectively; and means for calculating the density $\rho(r)$ and the individual molecular mass fraction $X_1(r), X_2(r), X_3(r) \ldots X_n(r)$ of each of the n constituent molecular components of the object at said each height $t_i$ of the beam in accordance with a separate one of the attenuation coefficients $\mu_1, \mu_2 \ldots \mu_{n-1}$, respectively.

6. The invention according to claim 5 wherein said scanning means comprises:

a radiation source for producing a beam containing photons, each having a distinct energy within at least one of said $n-1$ energy groups; and means for moving said radiation source relative to the object so that the beam of photons produced by said radiation source is scanned across the object.

7. The invention according to claim 6 wherein said intensity measuring means comprises:

a detector carried by said moving means for detecting the number of photons exiting the object and the energy of each; and a pulse height scaler/analyzer coupled to said detector for counting the number of photons impinging on said detector and for determining in which of the $n-1$ energy groups each photon belongs.

8. The invention according to claim 5 wherein said attenuation factor establishing means and said calculating means are comprised of a digital computer.

* * * * *